(12) United States Patent
Grombacher et al.

(10) Patent No.: US 6,734,345 B1
(45) Date of Patent: May 11, 2004

(54) CANOLA LINE 44A04

(75) Inventors: Alan Wall Grombacher, Beaumont (CA); Jayantilal D. Patel, Thornhill (CA)

(73) Assignee: Pioneer Hi-Bred International, Inc., Johnston, IA (US)

( * ) Notice: Subject to any disclaimer, the term of this patent is extended or adjusted under 35 U.S.C. 154(b) by 0 days.

(21) Appl. No.: 10/056,651

(22) Filed: Jan. 25, 2002

(51) Int. Cl.[7] .............................. A01H 5/00; A01H 5/10; A01H 1/02; C12N 5/04

(52) U.S. Cl. ...................... 800/306; 800/260; 800/274; 435/410; 435/430

(58) Field of Search .............................. 536/23.1, 23.6, 536/243; 435/4, 410, 419, 421, 430; 800/260, 264, 265, 266, 267, 268, 271, 274, 278, 287, 298, 299, 301, 302, 306

(56) References Cited

U.S. PATENT DOCUMENTS

| | | | |
|---|---|---|---|
| 5,523,520 A | * 6/1996 | Hunsperger et al. | ........ 435/410 |
| 5,750,871 A | * 5/1998 | Moloney et al. | ......... 435/252.2 |
| 6,288,307 B1 | 9/2001 | Patel | |
| 2001/0037515 A1 | 11/2001 | Patel | |

OTHER PUBLICATIONS

Bennetzen et al. 1992. Approaches and progress in the molecular cloning of plant disease resistance genes. Genetic Engineering 14:99–124.*

Earle et al. 1994. Cold–tolerant Ogura CMS Brassica vegetables for horticultural use. Cruciferae Newsletter 16:80–81.*

Eshed et al. 1994. Less–than–additive epistatic interactions of quantitative trait loci in tomato. Genetics 143:1807–1817.*

Goring et al. 1993. An S receptor kinase gene in self–compatible *Brassica napus* has a 1–bp deletion. The Plant Cell 5:531–539.*

Hemmat et al. 1998. Molecular markers for the scab resistance region in apple. J. Amer. Soc. Hort. Sci. 123(6):992–996.*

Kraft et al. 2000. Linkage disequilibrium and fingerprinting in sugar beet. Theor. Appl. Genet. 323–326.*

Michelmore et al. 1991. Identification of markers linked to disease–resistance genes by bulked segregant analysis: a rapid method to detect markers in specific genomic regions by using segregating populations. Proc. Natl. Acad. Sci. (USA):88:9828–9832.* van Ooijen et al. 1994. An RFLP linkage map of *Lycopersicon peruvianum*. Theor. Appl. Genet. 89:1007–1013.*

Pang et al. 1992. Expression of a gene encoding scorpion insectotoxin peptide in yeast, bacteria, and plants. Gene 116:165–172.*

* cited by examiner

*Primary Examiner*—Elizabeth F. McElwain
(74) *Attorney, Agent, or Firm*—McKee, Voorhees & Sease, P.L.C.

(57) ABSTRACT

A canola line designated 44A04, plants and seeds of the 44A04 canola line, methods for producing a canola plant produced by crossing the 44A04 line with itself or with another canola plant, and hybrid canola seeds and plants produced by crossing the 44A04 line with another canola line or plant are provided.

7 Claims, No Drawings

CANOLA LINE 44A04

FIELD OF THE INVENTION

The invention is in the field of *Brassica napus* breeding (i.e., canola breeding), specifically relating to the canola line designated 44A04.

BACKGROUND OF THE INVENTION

The present invention relates to a novel rapeseed line designated 44A04 is which is the result of years of careful breeding and selection. Since such line is of high quality and possesses a relatively low level of erucic acid in the vegetable oil component and a relatively low level of glucosinolate content in the meal component. It can be termed "canola" in accordance with the terminology commonly used by plant scientists.

The goal of plant breeding is to combine in a single variety or hybrid various desirable traits. For field crops, these traits may include resistance to diseases and insects, tolerance to heat and drought, reducing the time to crop maturity, greater yield, and better agronomic quality. With mechanical harvesting of many crops, uniformity of plant characteristics such as germination and stand establishment, growth rate, maturity, and plant and pod height, is important.

Field crops are bred through techniques that take advantage of the plant's method of pollination. A plant is self-pollinated if pollen from one flower is transferred to the same or another flower of the same plant. A plant is sib-pollinated when individuals within the same family or line are used for pollination. A plant is cross-pollinated if the pollen comes from a flower on a different plant from a different family or line. The term "cross-pollination" used herein does not include self-pollination or sib-pollination.

The creation of new superior, agronomically sound, and stable high yielding cultivars of many plant types including canola has posed an ongoing challenge to plant breeders. In the practical application of a chosen breeding program, the breeder often initially selects and crosses two or more parental lines, followed by repeated selfing and selection, thereby producing many unique genetic combinations. The breeder can theoretically generate billions of different genetic combinations via crossing, selfing and mutagenesis. However, the breeder commonly has no direct control at the cellular level of the plant. Therefore, two breeders will never independently develop the same line having the same canola traits.

Each year, the plant breeder selects the germplasm to advance to the next generation. This germplasm is grown under unique and different geographical, climatic and soil conditions, and further selections are then made during and at the end of the growing season. The characteristics of the lines developed are incapable of prediction in advance. This unpredictability is because the selection occurs in unique environments, with no control at the DNA level (using conventional breeding procedures), and with millions of different possible genetic combinations being generated. A breeder of ordinary skill cannot predict in advance the final resulting lines that are to be developed, except possibly in a very gross and general fashion. Even the same breeder is incapable of producing the same line twice by using the same original parents and the same selection techniques. This unpredictability commonly results in the expenditure of large research monies and effort to develop a new and superior canola line.

Canola breeding programs utilize techniques such as mass and recurrent selection, backcrossing, pedigree breeding and haploidy. For a general description of rapeseed and Canola breeding, see R. K. Downey and G. F. W. Rakow, 1987: Rapeseed and Mustard. In: Fehr, W. R. (ed.), Principles of Cultivar Development, 437–486. New York: Macmillan and Co.; Thompson, K. F., 1983: Breeding winter oilseed rape *Brassica napus*. Advances in Applied Biology 7: 1–104; and Oilseed Rape, Ward, et. al., Farming Press Ltd. , Wharefedale Road, Ipswich, Suffolk (1985), each of which are hereby incorporated by reference.

Recurrent selection is used to improve populations of either self- or cross-pollinating Brassica. Through recurrent selection, a genetically variable population of heterozygous individuals is created by intercrossing several different parents. The best plants are selected based on individual superiority, outstanding progeny, or excellent combining ability. The selected plants are intercrossed to produce a new population in which further cycles of selection are continued. Various recurrent selection techniques are used to improve quantitatively inherited traits controlled by numerous genes. Breeding programs use backcross breeding to transfer genes for a simply inherited, highly heritable trait into another line that serves as the recurrent parent. The source of the trait to be transferred is called the donor parent. After the initial cross, individual plants possessing the desired trait of the donor parent are selected and are crossed (backcrossed) to the recurrent parent for several generations. The resulting plant is expected to have the attributes of the recurrent parent and the desirable trait transferred from the donor parent. This approach has been used for breeding disease resistant phenotypes of many plant species, and has been used to transfer low erucic acid and low glucosinolate content into lines and breeding populations of Brassica.

Pedigree breeding and recurrent selection breeding methods are used to develop lines from breeding populations. Pedigree breeding starts with the crossing of two genotypes, each of which may have one or more desirable characteristics that is lacking in the other or which complements the other. If the two original parents do not provide all of the desired characteristics, other sources can be included in the breeding population. In the pedigree method, superior plants are selfed and selected in successive generations. In the succeeding generations the heterozygous condition gives way to homogeneous lines as a result of self-pollination and selection. Typically in the pedigree method of breeding five or more generations of selfing and selection is practiced: $F_1$ to $F_2$; $F_2$ to $F_3$; $F_3$ to $F_4$; $F_4$ to $F_5$, etc. For example, two parents that are believed to possess favorable complementary traits are crossed to produce an $F_1$. An $F_2$ population is produced by selfing one or several $F_1$'s or by intercrossing two $F_1$'s (i.e., sib mating). Selection of the best individuals may begin in the $F_2$ population, and beginning in the $F_3$ the best individuals in the best families are selected. Replicated testing of families can begin in the $F_4$ generation to improve the effectiveness of selection for traits with low heritability. At an advanced stage of inbreeding (i.e., $F_6$ and $F_7$), the best lines or mixtures of phenotypically similar lines commonly are tested for potential release as new cultivars. Backcrossing may be used in conjunction with pedigree breeding; for example, a combination of backcrossing and pedigree breeding with recurrent selection has been used to incorporate blackleg resistance into certain cultivars of *Brassica napus*.

Plants that have been self-pollinated and selected for type for many generations become homozygous at almost all gene loci and produce a uniform population of true breeding progeny. If desired, the haploidy method can also be used to extract homogeneous lines. A cross between two different homozygous lines produces a uniform population of hybrid plants that may be heterozygous for many gene loci. A cross of two plants each heterozygous at a number of gene loci will produce a population of hybrid plants that differ genetically and will not be uniform.

The choice of breeding or selection methods depends on the mode of plant reproduction, the heritability of the trait(s) being improved, and the type of cultivar used commercially (e.g., $F_1$ hybrid line, open pollinated variety, etc.) A true breeding homozygous line can also be used as a parental line (inbred line) in a commercial hybrid. If the line is being developed as an inbred for use in a hybrid, an appropriate pollination control system should be incorporated in the line. Suitability of an inbred line in a hybrid combination will depend upon the combining ability (general combining ability or specific combining ability) of the inbred.

Various breeding procedures are also utilized with these breeding and selection methods. The single-seed descent procedure in the strict sense refers to planting a segregating population, harvesting a sample of one seed per plant, and using the one-seed sample to plant the next generation. When the population has been advanced from the $F_2$ to the desired level of inbreeding, the plants from which lines are derived will each trace to different $F_2$ individuals. The number of plants in a population declines each generation due to failure of some seeds to germinate or some plants to produce at least one seed. As a result, not all of the $F_2$ plants originally sampled in the population will be represented by a progeny when generation advance is completed.

In a multiple-seed procedure, canola breeders commonly harvest one or more pods from each plant in a population and thresh them together to form a bulk. Part of the bulk is used to plant the next generation and part is put in reserve. The procedure has been referred to as modified single-seed descent or the pod-bulk technique.

The multiple-seed procedure has been used to save labor at harvest. It is considerably faster to thresh pods with a machine than to remove one seed from each by hand for the single-seed procedure. The multiple-seed procedure also makes it possible to plant the same number of seeds of a population each generation of inbreeding. Enough seeds are harvested to make up for those plants that did not germinate or produce seed. If desired the haploidy method can be used to extract homogeneous lines.

Molecular markers including techniques such as Isozyme Eletrophoresis, Restriction Fragment Length Polymorphisms (RFLPs), Randomly Amplified Ploymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) and Single Nucleotide Polymorphisms (SNPs) may be used in plant breeding methods. One use of molecular markers is Quantitative Trait Loci (QTL) mapping. QTL mapping is the use of markers, which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select for the genome of the recurrent parent and against the markers of the donor parent. Using this procedure can minimize the amount of genome from the donor parent that remains in the selected plants. It can also be used to reduce the number of crosses back to the recurrent parent needed in a backcrossing program. The use of molecular markers in the selection process is often called Genetic Marker Enhanced Selection or Marker Assisted Selection (MAS).

The production of double haploids can also be used for the development of inbreds in the breeding program. In *Brassica napus*, microspore culture technique is used in producing haploid embryos. The haploid embryos are then regenerated on appropriate media as haploid plantlets, doubling chromosomes of which results in doubled haploid plants. This can be advantageous because the process omits the generations of selfing needed to obtain a homogygous plant from a heterozygous source.

A pollination control system and effective transfer of pollen from one parent to the other offers improved plant breeding and an effective method for producing hybrid canola seed and plants. For example, the ogura cytoplasmic male sterility (cms) system, developed via protoplast fusion between radish (*Raphanus sativus*) and rapeseed (*Brassica napus*) is one of the most frequently used methods of hybrid production. It provides stable expression of the male sterility trait (Ogura 1968), Pelletier et al. (1983) and an effective nuclear restorer gene (Heyn 1976).

In developing improved new Brassica hybrid varieties, breeders use self-incompatible (SI), cytoplasmic male sterile (CMS) and nuclear male sterile (NMS) Brassica plants as the female parent. In using these plants, breeders are attempting to improve the efficiency of seed production and the quality of the $F_1$ hybrids and to reduce the breeding costs. When hybridization is conducted without using SI, CMS or NMS plants, it is more difficult to obtain and isolate the desired traits in the progeny ($F_1$ generation) because the parents are capable of undergoing both cross-pollination and self-pollination. If one of the parents is a SI, CMS or NMS plant that is incapable of producing pollen, only cross pollination will occur. By eliminating the pollen of one parental variety in a cross, a plant breeder is assured of obtaining hybrid seed of uniform quality, provided that the parents are of uniform quality and the breeder conducts a single cross.

In one instance, production of $F_1$ hybrids includes crossing a CMS Brassica female parent, with a pollen producing male Brassica parent. To reproduce effectively, however, the male parent of the $F_1$ hybrid must have a fertility restorer gene (Rf gene). The presence of a Rf gene means that the $F_1$ generation will not be completely or partially sterile, so that either self-pollination or cross pollination may occur. Self pollination of the $F_1$ generation to produce several subsequent generations is important to ensure that a desired trait is heritable and stable and that a new variety has been isolated.

An example of a Brassica plant which is cytoplasmic male sterile and used for breeding is ogura (OGU) cytoplasmic male sterile (R. Pellan-Delourme et al., 1987). A fertility restorer for ogura cytoplasmic male sterile plants has been transferred from *Raphanus sativus* (radish) to Brassica by Instit. National de Recherche Agricole (INRA) in Rennes, France (Pelletier et al., 1987). The restorer gene, Rf1 originating from radish, is described in WO 92/05251 and in Delourme et al., (1991). Improved versions of this restorer have been developed. For example, see WO98/27806 Oilseed brassica containing an improved fertility restorer gene for ogura cytoplasmic male sterility which is hereby incorporated by reference.

Other sources and refinements of CMS sterility in canola include the Polima cytoplasmic male sterile plant, as well as those of U.S. Pat. No. 5,789,566, DNA sequence imparting cytoplasmic male sterility, mitochondrial genome, nuclear genome, mitochondria and plant containing said sequence and process for the preparation of hybrids; U.S. Pat. No. 5,973,233 Cytoplasmic male sterility system production canola hybrids; and WO97/02737 Cytoplasmic male sterility system producing canola hybrids; EP patent application 0 599042A Methods for introducing a fertility restorer gene and for producing F1 hybrids of Brassica plants thereby; U.S. Pat. No. 6,229,072 Cytoplasmic male sterility system production canola hybrids; U.S. Pat. No. 4,658,085 Hybridization using cytoplasmic male sterility, cytoplasmic herbicide tolerance, and herbicide tolerance from nuclear genes; all of which are incorporated herein.

Promising advanced breeding lines commonly are tested and compared to appropriate standards in environments representative of the commercial target area(s). The best lines are candidates for new commercial lines; and those still deficient in a few traits may be used as parents to produce new populations for further selection.

For most traits the true genotypic value may be masked by other confounding plant traits or environmental factors. One method for identifying a superior plant is to observe its performance relative to other experimental plants and to one or more widely grown standard lines. If a single observation is inconclusive, replicated observations provide a better estimate of the genetic worth.

Proper testing should detect any major faults and establish the level of superiority or improvement over current lines. In addition to showing superior performance, there must be a demand for a new line that is compatible with industry standards or which creates a new market. The introduction of a new line commonly will incur additional costs to the seed producer, the grower, the processor and the consumer, for special advertising and marketing, altered seed and commercial production practices, and new product utilization. The testing preceding release of a new line should take into consideration research and development costs as well as technical superiority of the final line. For seed-propagated lines, it must be feasible to produce seed easily and economically.

These processes, which lead to the final step of marketing and distribution, usually take from approximately six to twelve years from the time the first cross is made. Therefore, the development of new lines such as that of the present invention is a time-consuming process that requires precise forward planning, efficient use of resources, and a minimum of changes in direction.

Further, as a result of the advances in sterility systems, lines are developed that can be used as an open pollinated variety (ie. a pureline cultivar sold to the grower for planting) and/or as a sterile inbred (female) used in the production of F1 hybrid seed. In the latter case, favorable combining ability with a restorer (male) would be desirable. The resulting hybrid seed would then be sold to the grower for planting.

The development of a canola hybrid in a canola plant breeding program involves three steps: (1) the selection of plants from various germplasm pools for initial breeding crosses; (2) the selfing of the selected plants from the breeding crosses for several generations to produce a series of inbred lines, which, although different from each other, breed true and are highly uniform; and (3) crossing the selected inbred lines with different inbred lines to produce the hybrids. During the inbreeding process in canola, the vigor of the lines decreases. Vigor is restored when two different inbred lines are crossed to produce the hybrid. An important consequence of the homozygosity and homogeneity of the inbred lines is that the hybrid between a defined pair of inbreds will always be the same. Once the inbreds that give a superior hybrid have been identified, the hybrid seed can be reproduced indefinitely as long as the homogeneity of the inbred parents is maintained.

Combining ability of a line, as well as the performance of the line per se, is a factor in the selection of improved canola lines that may be used as inbreds.

Combining ability refers to a line's contribution as a parent when crossed with other lines to form hybrids. The hybrids formed for the purpose of selecting superior lines are designated test crosses. One way of measuring combining ability is by using breeding values. Breeding values are based on the overall mean of a number of test crosses. This mean is then adjusted to remove environmental effects and it is adjusted for known genetic relationships among the lines.

Hybrid seed production requires inactivation of pollen produced by the female parent. Incomplete inactivation of the pollen provides the potential for self-pollination. This inadvertently self-pollinated seed may be unintentionally harvested and packaged with hybrid seed. Similarly, because the male parent is grown next to the female parent in the field there is also the potential that the male selfed seed could be unintentionally harvested and packaged with the hybrid seed. Once the seed from the hybrid bag is planted, it is possible to identify and select these self-pollinated plants. These self-pollinated plants will be genetically equivalent to one of the inbred lines used to produce the hybrid. Though the possibility of inbreds being included in hybrid seed bags exists, the occurrence is rare because much care is taken to avoid such inclusions. These self-pollinated plants can be identified and selected by one skilled in the art, either through visual or molecular methods.

*Brassica napus* canola plants, absent the use of sterility systems, are recognized to commonly be self-fertile with approximately 70 to 90 percent of the seed normally forming as the result of self-pollination. The percentage of cross pollination may be further enhanced when populations of recognized insect pollinators at a given growing site are greater. Thus open pollination is often used in commercial canola production.

Currently *Brassica napus* canola is being recognized as an increasingly important oilseed crop and a source of meal in many parts of the world. The oil as removed from the seeds commonly contains a lesser concentration of endogenously formed saturated fatty acids than other vegetable oils and is well suited for use in the production of salad oil or other food products or in cooking or frying applications. The oil also finds utility in industrial applications. Additionally, the meal component of the seeds can be used as a nutritious protein concentrate for livestock.

Canola oil has the lowest level of saturated fatty acids of all vegetable oils. "Canola" refers to rapeseed (Brassica) which as an erucic acid ($C_{22:1}$) content of at most 2 percent by weight based on the total fatty acid content of a seed, preferably at most 0.5 percent by weight and most preferably essentially 0 percent by weight and which produces, after crushing, an air-dried meal containing less than 30 micromoles (μmol) per gram of defatted (oil-free) meal. These types of rapeseed are distinguished by their edibility in comparison to more traditional varieties of the species.

SUMMARY OF THE INVENTION

According to the present invention, there is provided a novel *Brassica napus* line designated 44A04. This invention thus relates to the seeds of the 44A04 line, to plants of the 44A04 line, and to methods for producing a canola plant produced by crossing the 44A04 line with itself or another canola plant (whether by use of male sterility or open pollination), and to methods for producing a canola plant containing in its genetic material one or more transgenes and to transgenic plants produced by that method. This invention also relates to hybrid canola seeds and plants produced by crossing the line 44A04 with another line.

DEFINITIONS

In the description and tables which follow a number of terms are used. In order to aid in a clear and consistent understanding of the specification the following definitions and evaluation criteria are provided.

Type. This refers to whether the new line is considered to be primarily a Spring or Winter type of canola.

Ploidy. This refers to whether the number of chromosomes exhibited by the line is diploid or tetraploid.

Cotyledon. A cotyledon is a type of seed leaf; a small leaf contained on a plant embryo. A cotyledon contains the food storage tissues of the seed. The embryo is a small plant contained within a mature seed.

Cotyledon Length. The distance between the indentation at the top of the cotyledon and the point where the width of the petiole is approximately 4 mm.

Cotyledon Width. The width at the widest point of the cotyledon when the plant is at the two to three-leaf stage of development (mean of 50).

Leaf Color. The leaf blade coloration is observed when at least 6 leaves of the plant are completely developed.

Leaf Attachment to Stem. The presence or absence of clasping where the leaf attaches the stem, and when present the degree thereof are observed.

Leaf Glaucousity. The presence or absence of a fine whitish powdery coating on the surface of the leaves, and the degree thereof when present are observed.

Leaf Lobes. The fully developed upper stem leaves are observed for the presence or absence of leaf lobes when at least 6 leaves of the plant are completely developed.

Number of Leaf Lobes. The frequency of leaf lobes when present is observed when at least 6 leaves of the plant are completely developed.

Leaf Surface. The leaf surface is observed for the presence or absence of wrinkles when at least 6 leaves of the plant are completely developed.

Leaf Dentation. The margins of the upper stem leaves are observed for the presence or absence of indentation or serration, and the degree thereof if present when at least 6 leaves of the plant are completely developed.

Leaf Length. The length of the leaf blades and petioles are observed when at least 6, leaves of the plant are completely developed (mean of 50).

Leaf Width. The width of the leaf blades are observed when at least 6 leaves of the plant are completely developed (mean of 50).

Leaf Margin Hairiness. The leaf margins of the first leaf are observed for the presence or absence of pubescence, and the degree thereof when the plant is at the two leaf-stage.

Leaf Upper Side Hairiness. The upper surfaces of the leaves are observed for the presence or absence of hairiness, and the degree thereof if present when at least 6 of the leaves of the plant are formed.

Leaf Attitude. The disposition of typical leaves with respect to the petiole is observed when at least 6 leaves. of the plant are formed.

Leaf Tip Reflexion. The presence or absence of bending of typical leaf tips and the degree thereof, if present are observed at the 6 to 11 leaf-stage.

Leaf Anthocyanin Coloration. The presence or absence of leaf anthocyanin coloration and the degree thereof if present are observed when the plant has reached the 9 to 11 leaf-stage.

Petiole Length. The length of the petioles is observed in a line forming lobed leaves when at least 6 leaves of the plant are completely developed.

Stem Anthocyanin Coloration. The presence or absence of leaf anthocyanin coloration and the intensity thereof if present are observed when the plant has reached the 9 to 11 leaf-stage.

Speed of Root Formation. The typical speed of root formation is observed when the plant has reached the 4 to 11 leaf-stage.

Root Depth in Soil. The typical root depth is observed when the plant has reached at least the 6 leaf-stage.

Root Chlorophyll Coloration. The presence or absence of chlorophyll coloration in the skin at the top of the root is observed when the plant has reached at least the 6 leaf-stage.

Root Anthocyanin Coloration. The presence or absence of anthocyanin coloration in the skin at the top of the root is observed when the plant has reached at least the 6 leaf-stage.

Root Anthocyanin Expression. When anthocyanin coloration is present in skin at the top of the root, it further is observed for the exhibition of a reddish or bluish cast within such coloration when the plant has reached at least the 6 leaf-stage.

Root Anthocyanin Streaking. When anthocyanin coloration is present in the skin at the top of the root, it further is observed for the presence or absence of streaking within such coloration when the plant has reached at least the 6 leaf-stage.

Root Coloration Below Ground. The coloration of the root skin below ground is observed when the plant has reached at least the 6 leaf-stage.

Root Flesh Coloration. The internal coloration of the root flesh is observed when the plant has reached at least the 6 leaf-stage.

Seedling Growth Habit. The growth habit of young seedlings is observed for the presence of a weak (1) or strong (9) rosette character and is expressed on a scale of 1 to 9.

Plant Height. The overall plant height at the end of flowering is observed (mean of 50).

Time of Flowering. A determination is made of the number of days when at least 50 percent of the plants have one or more open buds on a terminal raceme in the year of sowing.

Flower Bud Location. A determination is made whether typical buds are disposed above or below the most recently opened flowers.

Flower Petal Coloration. The coloration of open exposed petals on the first day of flowering is observed.

Petal Length. The lengths of typical petals of fully opened flowers are observed (mean of 50).

Petal Width. The widths of typical petals of fully opened flowers are observed (mean of 50).

Anther Dotting. The level of anther dotting when the flowers are fully opened is observed.

Anther Arrangement. The general disposition of the anthers in typical fully opened flowers is observed.

Pollen Formation. The relative level of pollen formation is observed at the time of dehiscence.

Pod Type. The overall configuration of the silique is observed.

Pod Length. The typical silique length is observed and is expressed on a scale of 1 (short) to 5 (long).

Pod Width. The typical silique width when mature is observed and is expressed on a scale of 1 (narrow) to 5 (wide).

Pedicel Length. The typical length of the silique peduncle when mature is observed and is expressed on a scale of 1 (short) to 5 (long).

Length of Beak. The typical length of the silique beak when mature is observed and is expressed on a scale of 1 (short) to 5 (long).

Pod Anthocyanin Coloration. The presence or absence at maturity of silique anthocyanin coloration, and the degree thereof if present are observed.

Pod Habit. The typical manner in which the silique are borne on the plant at maturity is observed.

Maturity. The number of days from planting to maturity is observed with maturity being defined as the plant stage when pods with seed color change, occurring from green to brown or black, on the bottom third of the pod bearing area of the main stem.

Seeds Per Pod. The average number of seeds per pod is observed (mean of 50).

Seed Size. The weight in grams of 1,000 typical seeds is determined at maturity while such seeds exhibit a moisture content of approximately 5 to 6 percent by weight.

Seed Coat Color. The seed coat color of typical mature seeds is observed.

Seed Coat Mucilage. The presence or absence of mucilage on the seed coat is determined and is expressed on a scale of 1 (absent) to 9 (heavy). During such determination a petri dish is filled to a depth of 0.3 cm. with tap water provided at room temperature. Seeds are added to the petri dish and are immersed in water where they are allowed to stand for five minutes. The contents of the petri dish containing the immersed seeds next is examined under a stereo microscope equipped with transmitted light. The presence of mucilage and the level thereof is observed as the intensity of a halo surrounding each seed.

Oil Content: The typical percentage by weight oil present in the mature whole dried seeds is determined by ISO 10565:1993 Oilseeds Simultaneous determination of oil and water—Pulsed NMR method. Also, oil could be analyzed using NIR (Near Infra Red sprectoscopy) as long as the instrument is calibrated and certified by Grain Research Laboratory of Canada.

Protein Content: The typical percentage by weight of protein in the oil free meal of the mature whole dried seeds is determined by AOCS Official Method Ba 4e-93 Combustion Method for the Determination of Crude Protein. Also, protein could be analyzed using NIR (Near Infra Red sprectoscopy) as long as the instrument is calibrated and certified by Grain Research Laboratory of Canada.

Fatty Acid Content: The typical percentages by weight of fatty acids present in the endogenously formed oil of the mature whole dried seeds are determined. During such determination the seeds are crushed and are extracted as fatty acid methyl esters following reaction with methanol and sodium methoxide. Next the resulting ester is analyzed for fatty acid content by gas liquid chromatography using a capillary column which allows separation on the basis of the degree of unsaturation and fatty acid chain length. This procedure is described in the work of J. K. Daun et al. *J. Amer. Oil Chem. Soc.*, 60: 1751 to 1754 (1983) which is herein incorporated by reference.

Chlorophyll Content. The typical chlorophyll content of the mature seeds is determined by using methods recommended by the WCC/RRC and is considered to be low if <8 ppm, medium if 8 to 15 ppm, and high if 15 to 30 ppm.

Glucosinolate Content. The total glucosinolates of seed at 8.5% moisture as measured by AOCS Official Method AK-1-92 (Determination of glucosinolates content in rapeseed-colza by HPLC) is expressed micromoles per gram. Capillary gas chromatography of the trimethylsityl derivatives of extracted and purified desulfoglucosinolates with optimization to obtain optimum indole glucosinolate detection as described in "Procedures of the Western Canada Canola/Rapeseed Recommending Committee Incorporated for the Evaluation and Recommendation for Registration of Canola/Rapeseed Candidate Cultivars in Western Canada".

Resistance to Shattering. Resistance to silique shattering is observed at seed maturity and is expressed on a scale of 1 (poor) to 9 (excellent).

Resistant to Lodging. Resistance to lodging at the maturity and is expressed on a scale of 1 (weak) to 9 (strong).

Frost Tolerance (Spring Type Only). The ability of young plants to withstand late spring frosts at a typical growing area is evaluated and is expressed on a scale of 1 (poor) to 5 (excellent).

Winter Survival (Winter Type Only). The ability to withstand winter temperatures at a typical growing area is evaluated and is expressed on a scale of 1 (poor) to 5 (excellent).

Disease Resistance: Resistant to various diseases is evaluated and is expressed on a scale of 0 highly resistant, 5=highly susceptible. The WCC/RRC blackleg classification is based on % severity index described as follows:

0–30%=Resistant

30%–50%=Moderately Resistant

50%–70%=Moderately Susceptible

70%–90%=Susceptible

>90%=Highly susceptible.

The % severity index=blackleg rating on 0–5 for a variety/blackleg rating for HS variety Westar.

Herbicide Resistance: Resistance to various herbicides when applied at standard recommended application rates is expressed on a scale of 1 (resistant), 2 (tolerant), or 3 (susceptible).

DETAILED DESCRIPTION OF THE INVENTION

A canola line needs to be homogenous, homozygous and reproducible to be useful for the production of a commercial crop on a reliable basis or for use as an inbred line. There are a number of analytical methods available to determine the homozygotic and phenotypic stability of a canola line.

The oldest and most traditional method of analysis is the observation of phenotypic traits. The data is usually collected in field experiments over the life of the canola plants to be examined. Phenotypic characteristics most often are observed for traits associated with seed yield, seed oil content, seed protein content, fatty acid composition of oil, glucosinolate content of meal, growth habit, lodging resistance, plant height, shattering resistance, etc.

In addition to phenotypic observations, the genotype of a plant can also be examined. A plant's genotype can be used to identify plants of the same variety or a related variety. For example, the genotype can be used to determine the pedigree of a plant. There are many laboratory-based techniques available for the analysis, comparison and characterization of plant genotype; among these are Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length Polymorphisms (AFLPs), Simple Sequence Repeats (SSRs) which are also referred to as Microsatellites, and Single Nucleotide Polymorphisms (SNPs).

The line of the present invention has shown uniformity and stability for all traits, as described in the following line description information. It has been self-pollinated a sufficient number of generations, with careful attention to uniformity of plant type to ensure homozygosity. and phenotypic stability. The line has been increased with continued observation for uniformity. The frequency of variants in this variety is less than 1/10,000.

Line 44A04 is an improved blackleg resistant (rating=R) spring canola variety demonstrating very high yield, early maturity, very low green seed, very high oil content, high protein content, short plant stature and good saturate levels. The line is best adapted for and performs consistently in Canada, particularly the short season zone of the Western Canadian provinces of Manitoba, Saskatchewan, Alberta and British Columbia.

Morphological

Since canola line 44A04 is substantially homogeneous, it can be reproduced by planting seeds of such line, growing the resulting canola plants under self-pollinating or sib-pollinating conditions with adequate isolation, and harvesting the resulting seed using conventional agronomic practices. Sterile versions (OGU-CMS or A line) of canola line 44A04 can be reproduced by pollination with the normal fertile of 44A04 (maintainer line or B line).

TABLE 1

VARIETY DESCRIPTION INFORMATION
44A04

1. Species: *Brassica napus*
2. Type: Spring
3. Plant Height:

102.05 cm Tall
   8.63 cm shorter than Defender
   4.92 cm shorter than Excel
   1.68 cm shorter than Legacy
   Height Class: Short (Spring sown)

4. Stem Anthocyanin:
5. Seed Cotyledons:

Width: 19.45 mm
   Length: 9.06 mm

TABLE 1-continued

VARIETY DESCRIPTION INFORMATION
44A04

6. Leaves:

Margin Type: 2.60
   Margin Depth: 4.75
   Length: 18.35 cm
   Width: 8.28 cm
   Lobing: 6.05
   Color: 2.08

7. Flowers:

Petiole length: 8.73 cm
   Petal color: 3.00
   Petal length: 16.18 mm
   Petal width: 7.80 mm
   Anther fertility: 2.00

8. Pods:

Silique attitude: 4.40
   Silique length: 62.83 mm
   Silique width: 5.17 mm
   Beak length: 10.69 mm
   Pedicel length: 22.32 mm
   Days to maturity: 109.89

9. Seeds:

Unsized seed:
   Weight class: 3.72 g/1000 seeds
   Seed coat color: 1.50

10. Chemical composition of seed:

Erucic acid: 0.03%
   Glucosinate content: 10.56 micro moles/g of seed at 8.5% $H_2O$
   Chlorophyll content: 22.6 ppm 11. Disease resistance:

Black Leg: 1.14
   White Rust: 1.00

Results are the average of the mean values measured in each year.

When preparing the detailed phenotypic information that follows, plants of the new 44A04 line were observed while growing using conventional agronomic practices. For comparative purposes canola plants of four publicly available canola lines were similarly grown in a three-replication experiment planted at the same location over two years. Results are the average of the mean values measured in each year.

Based on observations recorded on various morphological traits over two years for the line 44A04 and comparative check cultivars, line 44A04 can be described as follows:

The cotyledons are of medium width and long to very length. Leaf blades are medium green with a large percentage of rounded lobes which are medium in depth. The leaves are short to medium in length and medium in width with a medium petiole length. The medium yellow flower petals are of wide width and medium to long in length. The anthers shed pollen. The semi-erect to horizontal siliques are medium in width and medium in length with a medium to long beak length and a short to medium pedicel length. The plants are short and mature early. Seed colour is dark brown. '44A04' is resistant to blackleg (*Leptosphaeria maculans*) and white rust (Albugo candida races 2V and 7V).

TABLE 2

| MORPHOLOGICAL TRAIT | 44A04 | Defender | Excel | Legacy | 44A89 |
|---|---|---|---|---|---|
| Canola Type | Spring | Spring | Spring | Spring | Spring |
| cotyledon width (mm) | 19.45 | 18.56 | 19.96 | 18.64 | 18.84 |
| cotyledon length (mm) | 9.06 | 8.49 | 8.63 | 8.19 | 8.47 |
| leaf blade color | Medium green | Medium green | Medium green | Medium green | Medium green |
| leaf number of lobes | 6.05 | 6.20 | 5.65 | 6.07 | 6.12 |
| leaf margin type | Rounded | Rounded | Rounded | Rounded | Rounded |
| leaf depth of margin dent | Medium | Medium | Shallow to medium | Medium | Shallow to medium |
| leaf length (cm) | 18.35 | 19.55 | 19.87 | 19.58 | 18.23 |
| leaf width (cm) | 8.28 | 7.90 | 8.20 | 8.06 | 7.69 |
| Length:width ratio | 2.23 | 2.49 | 2.35 | 2.49 | 2.28 |
| leaf petiole length (cm) | 8.73 | 7.96 | 8.12 | 7.11 | 8.30 |
| Flower date 50% | 48.70 | 51.23 | 50.85 | 51.60 | 50.20 |
| petal color | Medium yellow | Medium yellow | Medium yellow | Medium yellow | Medium yellow |
| petal length (mm) | 16.18 | 15.09 | 15.21 | 15.69 | 15.13 |
| petal width (mm) | 7.80 | 7.22 | 7.26 | 7.69 | 7.54 |
| Length:width ratio | 2.09 | 2.08 | 2.11 | 2.07 | 2.03 |
| anther fertility | Shedding pollen | Shedding pollen | Shedding pollen | Shedding pollen | Shedding pollen |
| silique attitude (1 = erect, 9 = drooping) | 4.40 | 3.38 | 3.13 | 3.12 | 3.77 |
| silique length (mm) | 62.83 | 60.15 | 61.30 | 62.08 | 58.04 |
| silique width (mm) | 5.17 | 5.54 | 5.04 | 5.08 | 5.19 |
| beak length (mm) | 10.69 | 12.04 | 11.61 | 11.87 | 9.85 |
| pedicel length (mm) | 22.32 | 24.55 | 21.30 | 24.11 | 20.48 |
| Maturity (days from planting) | 109.89 | 113.48 | 113.68 | 114.99 | 112.13 |

FURTHER EMBODIMENTS OF THE INVENTION

This invention also is directed to methods for producing a canola plant by crossing a first parent canola plant with a second parent canola plant wherein either the first or second parent canola plant is a canola line 44A04. Further, both first and second parent canola plants can come from the canola line 44A04. Either the first or the second parent plant may be male sterile.

Still further, this invention also is directed to methods for producing a canola 44A04-derived canola plant by crossing canola line 44A04 with a second canola plant and growing the progeny seed, and repeating the crossing and growing steps with the canola 44A04-derived plant from 1 to 2 times, 1 to 3 times, 1 to 4 times, or 1 to 5 times. Thus, any such methods using the canola line 44A04 are part of this invention: open pollination, selfing, backcrosses, hybrid production, crosses to populations, and the like. All plants produced using canola line 44A04 as a parent are within the scope of this invention, including plants derived from canola line 44A04. This includes canola lines derived from 44A04 which include components for either male sterility or for restoration of fertility. Advantageously, the canola line is used in crosses with other, different, canola plants to produce first generation (F1) canola hybrid seeds and plants with superior characteristics.

A further embodiment of the invention is a single gene conversion of 44A04. A single gene conversion occurs when DNA sequences are introduced through traditional (non-transformation) breeding techniques, such as backcrossing). DNA sequences, whether naturally occurring or transgenes, may be introduced using these traditional breeding techniques. Desired traits transferred through this process include, but are not limited to, fertility restoration, fatty acid profile modification, other nutritional enhancements, industrial enhancements, disease resistance, insect resistance, herbicide resistance and yield enhancements. The trait of interest is transferred from the donor parent to the recurrent parent, in this case, the canola plant disclosed herein. Single gene traits may result from either the transfer of a dominant allele or a recessive allele. Selection of progeny containing the trait of interest is done by direct selection for a trait associated with a dominant allele. Selection of progeny for a trait that is transferred via a recessive allele, requires growing and selfing the first backcross to determine which plants carry the recessive alleles. Recessive traits may require additional progeny testing in successive backcross generations to determine the presence of the gene of interest.

It should be understood that the canola line of the invention can, through routine manipulation by cytoplasmic genes, nuclear genes, or other factors, be produced in a male-sterile or restorer form as described in the references discussed earlier. Such embodiments are also within the scope of the present claims. Canola line 44A04 can be manipulated to be male sterile by any of a number of methods known in the art, including by the use of mechanical methods, chemical methods, SI, CMS (either ogura or another system) or NMS. The term manipulated to be male sterile refers to the use of any available techniques to produce a male sterile version of canola line 44A04. The male sterility may be either partial or complete male sterility. This invention is also directed to F1 hybrid seed and plants produced by the use of Canola line 44A04. Canola line 44A04 can also further comprise a component for fertility restoration of a male sterile plant, such as an Rf restorer gene. In this case, canola line 44A04 could then be used as the male plant in hybrid seed production.

This invention is also directed to the use of 44A04 in tissue culture. As used herein, the term plant includes plant protoplasts, plant cell tissue cultures from which canola plants can be regenerated, plant calli, plant clumps, and plant cells that are intact in plants or parts of plants, such as embryos, pollen, ovules, seeds, flowers, kernels, ears, cobs, leaves, husks, stalks, roots, root tips, anthers, silk and the like. Pauls et al, confirmed that tissue culture as well as microspore culture for regeneration of canola plants can be accomplished successfully. Chuong et al., "A Simple Culture Method for Brassica hypocotyl Protoplasts", *Plant Cell Reports* 4:4–6 (1985); Barsby, T. L., et al., "A Rapid and Efficient Alternative Procedure for the Regeneration of Plants from Hypocotyl Protoplasts of *Brassica napus*", *Plant Cell Reports*, (Spring 1996); Kartha, K. et al., "In vitro Plant Formation from Stem Explants of Rape", *Physiol. Plant*, 31:217–220 (1974); Narasimhulu, S., et al., "Species Specific Shoot Regeneration Response of Cotyledonary Explants of Brassicas", *Plant Cell Reports*, (Spring 1988); Swanson, E., "Microspore Culture in Brassica", *Methods in Molecular Biology*, Vol. 6, Chapter 17, p. 159 (1990). "Cell Culture techniques and Canola improvement" J. Am. Oil Chem. Soc. 66, 4, 455–56, 1989. Thus, it is clear from the literature that the state of the art is such that these methods of obtaining plants are, and were, "conventional" in the sense that they are routinely used and have a very high rate of success.

The utility of canola line 44A04 also extends to crosses with other species. Commonly, suitable species will be of the family Brassicae.

The advent of new molecular biological techniques have allowed the isolation and characterization of genetic elements with specific functions, such as encoding specific protein products. Scientists in the field of plant biology developed a strong interest in engineering the genome of plants to contain and express foreign genetic elements, or additional, or modified versions of native or endogenous genetic elements in order to alter the traits of a plant in a specific manner. Any DNA sequences, whether from a different species or from the same species, that are inserted into the genome using transformation are referred to herein collectively as "transgenes". Over the last fifteen to twenty years several methods for producing transgenic plants have been developed, and the present invention, in particular embodiments, also relates to transformed versions of the claimed canola line 44A04.

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Genetic Transformation for the improvement of Canola World Conf., Biotechnol. Fats and Oils Ind. 43–46, 1988. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89–119.

The most prevalent types of plant transformation involve the construction of an expression vector. Such a vector comprises a DNA sequence that contains a gene under the control of or operatively linked to a regulatory element, for example a promoter. The vector may contain one or more genes and one or more regulatory elements.

A genetic trait which has been engineered into a particular canola plant using transformation techniques, could be moved into another line using traditional breeding techniques that are well known in the plant breeding arts. For example, a backcrossing approach could be used to move a transgene from a transformed canola plant to an elite inbred line and the resulting progeny would comprise a transgene. Also, if an. inbred line was used for the transformation then the transgenic plants could be crossed to a different line in order to produce a transgenic hybrid canola plant. As used herein, "crossing" can refer to a simple X by Y cross, or the process of backcrossing, depending on the context. Various genetic elements can be introduced into the plant genome using transformation. These elements include but are not limited to genes; coding sequences; inducible, constitutive, and tissue specific promoters; enhancing sequences; and signal and targeting sequences. See U.S. Pat. No. 6,222,101 which is herein incorporated by reference.

With transgenic plants according to the present invention, a foreign protein can be produced in commercial quantities. Thus, techniques for the selection and propagation of transformed plants, which are well understood in the art, yield a plurality of transgenic plants which are harvested in a conventional manner, and a foreign protein then can be extracted from a tissue of interest or from total biomass. Protein extraction from plant biomass can be accomplished by known methods which are discussed, for example, by Heney and Orr, *Anal. Biochem.* 114: 92–6 (1981).

A genetic map can be generated, primarily via conventional Restriction Fragment Length Polymorphisms (RFLP), Polymerase Chain Reaction (PCR) analysis, and Simple Sequence Repeats (SSR) which identifies the approximate chromosomal location of the integrated DNA molecule coding for the foreign protein. For exemplary methodologies in this regard, see Glick and Thompson, METHODS IN PLANT MOLECULAR BIOLOGY AND BIOTECHNOLOGY 269–284 (CRC Press, Boca Raton, 1993). Map information concerning chromosomal location is useful for proprietary protection of a subject transgenic plant. If unauthorized propagation is undertaken and crosses made with other germplasm, the map of the integration region can be compared to similar maps for suspect plants, to determine if the latter have a common parentage with the subject plant. Map comparisons would involve hybridizations, RFLP, PCR, SSR and sequencing, all of which are conventional techniques.

Likewise, by means of the present invention, plants can be genetically engineered to express various phenotypes of agronomic interest. Exemplary transgenes implicated in this regard include, but are not limited to, those categorized below.

1. Genes That Confer Resistance To Pests or Disease And That Encode (A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones et al., Science 266: 789 (1994) (cloning of the tomato Cf-9 gene for resistance to *Cladosporum fulvum*); Martin et al., Science 262: 1432 (1993) (tomato Pto gene for resistance to *Pseudomonas synngae* pv. tomato encodes a protein kinase); Mindrinos et al., Cell 78: 1089 (1994) (Arabidopsis RSP2 gene for resistance to *Pseudomonas syringae*).

(B) A gene conferring resistance to fungal pathogens, such as oxalate oxidase or oxalate decarboxylase (Zhou et al., Pl. Physiol. 117(1):33–41 (1998)).

(C) A *Bacillus thuringiensis* protein, a derivative thereof or a synthetic polypeptide modeled thereon. See, for example, Geiser et al., *Gene* 48: 109 (1986), who disclose the cloning and nucleotide sequence of a Bt δ-endotoxin gene. Moreover, DNA molecules encoding δ-endotoxin genes can be purchased from American Type Culture Collection (Manassas, Va.), for example, under ATCC Accession Nos. 40098, 67136, 31995 and 31998.

(D) A lectin. See, for example, the disclosure by Van Damme et al., *Plant Molec. Biol.* 24: 25 (1994), who disclose the nucleotide sequences of several *Clivia miniata* mannose-binding lectin genes.

(E) A vitamin-binding protein such as avidin. See PCT application U.S. 93/06487, the contents of which are hereby incorporated by reference. The application teaches the use of avidin and avidin homologues as larvicides against insect pests.

(F) An enzyme inhibitor, for example, a protease or proteinase inhibitor or an amylase inhibitor. See, for example, Abe et al., *J. Biol. Chem.* 262: 16793 (1987) (nucleotide sequence of rice cysteine proteinase inhibitor), Huub et al., *Plant Molec. Biol.* 21: 985 (1993) (nucleotide sequence of cDNA encoding tobacco proteinase inhibitor I), Sumitani et al., *Biosci. Biotech. Biochem.* 57: 1243 (1993) (nucleotide sequence of *Streptomyces nitrosporeus* α-amylase inhibitor) and U.S. Pat. No. 5,494,813 (Hepher and Atkinson, issued Feb. 27, 1996).

(G) An insect-specific hormone or pheromone such as an ecdysteroid and juvenile hormone, a variant thereof, a mimetic based thereon, or an antagonist or agonist thereof. See, for example, the disclosure by Hammock et al., Nature 344: 458 (1990), of baculovirus expression of cloned juvenile hormone esterase, an inactivator of juvenile hormone.

(H) An insect-specific peptide or neuropeptide which, upon expression, disrupts the physiology of the affected pest. For example, see the disclosures of Regan, *J. Biol. Chem.* 269: 9 (1994) (expression cloning yields DNA coding for insect diuretic hormone receptor), and Pratt et al., *Biochem. Biophys. Res. Comm.* 163: 1243 (1989) (an allostatin is identified in *Diploptera puntata*). See also U.S. Pat. No. 5,266,317 to Tomalski et al., who disclose genes encoding insect-specific, paralytic neurotoxins.

(I) An insect-specific venom produced in nature by a snake, a wasp, etc. For example, see Pang et al., *Gene* 116: 165 (1992), for disclosure of heterologous expression in plants of a gene coding for a scorpion insectotoxic peptide.

(J) An enzyme responsible for an hyperaccumulation of a monterpene, a sesquiterpene, a steroid, hydroxamic acid, a phenylpropanoid derivative or another non-protein molecule with insecticidal activity.

(K) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See PCT application WO 93/02197 in the name of Scott et al., which discloses the nucleotide sequence of a callase gene. DNA molecules which contain chitinase-encoding sequences can be obtained, for example, from the ATCC under Accession Nos. 39637 and 67152. See also Kramer et al., *Insect Biochem. Molec. Biol.* 23: 691 (1993), who teach the nucleotide sequence of a cDNA encoding tobacco hookworm chitinase, and Kawalleck et al., *Plant Molec. Biol.* 21: 673 (1993), who provide the nucleotide sequence of the parsley ubi4-2 polyubiquitin gene.

(L) A molecule that stimulates signal transduction. For example, see the disclosure by Botella et al., *Plant Molec. Biol.* 24: 757 (1994), of nucleotide sequences for mung bean calmodulin cDNA clones, and Griess et al., *Plant Physiol.* 104: 1467 (1994), who provide the nucleotide sequence of a maize calmodulin cDNA clone.

(M) A hydrophobic moment peptide. See PCT application WO95/16776 (disclosure of peptide derivatives of Tachyplesin which inhibit fungal plant pathogens) and PCT application WO95/18855 (teaches synthetic antimicrobial peptides that confer disease resistance), the respective contents of which are hereby incorporated by reference.

(N) A membrane permease, a channel former or a channel blocker. For example, see the disclosure by Jaynes et al., *Plant Sci.* 89: 43 (1993), of heterologous expression of a cecropin-β lytic peptide analog to render transgenic tobacco plants resistant to *Pseudomonas solanacearum*.

(O) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See Beachy et al., *Ann. Rev. Phytopathol.* 28: 451 (1990). Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(P) An insect-specific antibody or an immunotoxin derived therefrom. Thus, an antibody targeted to a critical metabolic function in the insect gut would inactivate an affected enzyme, killing the insect. Cf. Taylor et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments).

(Q) A virus-specific antibody. See, for example, Tavladoraki et al., *Nature* 366: 469 (1993), who show that transgenic plants expressing recombinant antibody genes are protected from virus attack.

(R) A developmental-arrestive protein produced in nature by a pathogen or a parasite. Thus, fungal endo α-1,4-D-polygalacturonases facilitate fungal colonization and plant nutrient release by solubilizing plant cell wall homo-α-1,4-D-galacturonase. See Lamb et al., *Bio/Technology* 10: 1436 (1992). The cloning and characterization of a gene which encodes a bean endopolygalacturonase-inhibiting protein is described by Toubart et al., *Plant J.* 2: 367 (1992).

(S) A developmental-arrestive protein produced in nature by a plant. For example, Logemann et al., *Bio/Technology* 10: 305 (1992), have shown that transgenic plants expressing the barley ribosome-inactivating gene have an increased resistance to fungal disease.

(T) Genes involved in the Systemic Acquired Resistance (SAR) Response and/or the pathogenesis related genes. Briggs, S., Current Biology, 5(2) (1995).

(U) Antifungal genes (Cornelissen and Melchers, Pl. Physiol. 101:709–712, (1993) and Parijs et al., Planta 183:258–264, (1991) and Bushnell et al., Can. J. of Plant Path. 20(2):137–149 (1998).

2. Genes That Confer Resistance to a Herbicide, for Example (A) A herbicide that inhibits the growing point or meristem, such as an imidazalinone or a sulfonylurea. Exemplary genes in this category code for mutant ALS and AHAS enzyme as described, for example, by Lee et al., EMBO J. 7: 1241 (1988), and Miki et al., Theor. Appl. Genet. 80: 449 (1990), respectively.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase, PAT) and Streptomyces hygroscopicus phosphinothricin-acetyl transferase, bar, genes), and pyridinoxy or phenoxy propionic acids and cycloshexones (ACCase inhibitor-encoding genes). See, for example, U.S. Pat. No. 4,940,835 to Shah et al., which discloses the nucleotide sequence of a form of EPSP which can confer glyphosate resistance. A DNA molecule encoding a mutant aroA gene can be obtained under ATCC accession No. 39256, and the nucleotide sequence of the mutant gene is disclosed in U.S. Pat. No. 4,769,061 to Comai. European patent application No. 0 333 033 to Kumada et al. and U.S. Pat. No. 4,975,374 to Goodman et al. disclose nucleotide sequences of glutamine synthetase genes which confer resistance to herbicides such as L-phosphinothricin. The nucleotide sequence of a phosphinothricin-acetyl-transferase gene is provided in European application No. 0 242 246 to Leemans et al. De Greef et al., Bio/Technology 7: 61 (1989), describe the production of transgenic plants that express chimeric bar genes coding for phosphinothricin acetyl transferase activity. Exemplary of genes conferring resistance to phenoxyi propionic acids and cycloshexones, such as sethoxydim and haloxyfop, are the Acc1-S1, Acc1-S2 and Acc1-S3 genes described by Marshall et al., Theor. Appl. Genet. 83: 435 (1992).

(C) A herbicide that inhibits photosynthesis, such as a triazine (psbA and gs+ genes) and a benzonitrile (nitrilase gene). Przibilla et al., Plant Cell 3: 169 (1991), describe the transformation of Chlamydomonas with plasmids encoding mutant psbA genes. Nucleotide sequences for nitrilase genes are disclosed in U.S. Pat. No. 4,810,648 to Stalker, and DNA molecules containing these genes are available under ATCC Accession Nos. 53435, 67441 and 67442. Cloning and expression of DNA coding for a glutathione S-transferase is described by Hayes et al., Biochem. J. 285: 173 (1992).

3. Genes That Confer or Contribute to a Value-Added Trait, Such as (A) Modified fatty acid metabolism, for example, by transforming a plant with an antisense gene of stearoyl-ACP desaturase to increase stearic acid content of the plant. See Knultzon et al., Proc. Nat'l. Acad. Sci. U.S.A 89: 2624 (1992).

(B) Decreased phytate content (1) Introduction of a phytase-encoding gene would enhance breakdown of phytate, adding more free phosphate to the transformed plant. For example, see Van Hartingsveldt et al., Gene 127: 87 (1993), for a disclosure of the nucleotide sequence of an Aspergillus niger phytase gene.

(2) A gene could be introduced that reduces phytate content. In maize, this, for example, could be accomplished, by cloning and then reintroducing DNA associated with the single allele which is responsible for maize mutants characterized by low levels of phytic acid. See Raboy et al., Maydica 35: 383 (1990).

(C) Modified carbohydrate composition effected, for example, by transforming plants with a gene coding for an enzyme that alters the branching pattern of starch. See Shiroza et al., J. Bacteriol. 170: 810 (1988) (nucleotide sequence of Streptococcus mutans fructosyltransferase gene), Steinmetz et al., Mol. Gen. Genet. 200: 220 (1985) (nucleotide sequence of Bacillus subtilis levansucrase gene), Pen et al., Bio/Technology 10: 292 (1992) (production of transgenic plants that express Bacillus licheniformis α-amylase), Elliot et al., Plant Molec. Biol. 21: 515 (1993) (nucleotide sequences of tomato invertase-genes), Søgaard et al., J. Biol. Chem. 268: 22480 (1993) (site-directed mutagenesis of barley α-amylase gene), and Fisher et al., Plant Physiol. 102: 1045 (1993) (maize endosperm starch branching enzyme II).

(D) Reduced green seed, by down regulation of the CAB gene in Canola seed (Abstract #1566, Am. Soc. Pl. Physiol. Meeting 1997, Morisette et al.

(E) Elevated oleic acid via FAD-2 gene modification and/or decreased linolenic acid via FAD-3 gene modification (see U.S. Pat. Nos. 6,063,947; 6,323,392; and WO 93/11245).

4. Genes That Control Pollination or Hybrid Seed Production (Canadian Patent Application 2,021,703, PHI Ref. 217-CA and PCT/CA98/00089, PHI Ref. 618P-PCT-CA.

Industrial Applicability

The seed of the 44A04 line, the plant produced from such seed, the hybrid canola plant produced from the crossing of the 44A04 line, the resulting hybrid seed, and various parts of the hybrid canola plant can be utilized in the production of an edible vegetable oil or other food products in accordance with known techniques. The remaining solid meal component derived from seeds can be used as a nutritious livestock feed.

Performance Examples of the 44A04 Line

Performance data for the new 44A04 line is presented hereafter.

Table 3 compares the agronomic traits of 44A04 to the same reference varieties earlier compared for morphological traits, namely, Defender, Excel, Legacy, and 44A89.

TABLE 3

| Trait | 44A04 | 44A89 | Defender | Legacy | Excel | # locations |
|---|---|---|---|---|---|---|
| yield (Kg/Ha) in SSZ | 3459.1 | 3124.7 | 3208.7 | 3160.8 | 3083.1 | 15.0 |
| maturity (days from planting) | 109.89 | 112.13 | 113.48 | 114.99 | 113.68 | 10.0 |
| plant height (cm) | 102.05 | 95.40 | 110.68 | 103.73 | 106.97 | 7.0 |
| seed weight (grams per 1000 seeds) | 3.72 | | 3.76 | 3.40 | 3.59 | 7.0 |
| oil % | 49.9 | 49.0 | 48.6 | 48.6 | 49.4 | 12.0 |
| protein % | 48.1 | 49.1 | 47.7 | 49.5 | 47.8 | 11.0 |
| erucic acid % of total fatty acids | 0.0 | 0.0 | 0.2 | 0.1 | 0.9 | 7.0 |
| total saturated fatty acids | 6.5 | 6.7 | 6.5 | 6.4 | 6.5 | 7.0 |
| glucosinolates | 10.5 | 11.6 | 13.0 | 11.2 | 19.2 | 7.0 |
| chlorophyll content | 22.6 | 22.6 | 35.8 | 37.2 | 49.8 | 7.0 |

TABLE 3-continued

| Trait | 44A04 | 44A89 | De-fender | Legacy | Excel | # loca-tions |
|---|---|---|---|---|---|---|
| greenseed | 0.4 | 0.1 | 0.4 | 1.3 | 1.6 | 7.0 |
| blackleg resistance* | 1.1 | | 1.9 | 2.8 | 2.6 | 7.0 |
| whiterust** | 1.0 | 1.0 | 1.0 | 1.0 | 1.0 | 1.0 |

+ blackleg reaction 0 = good, 5 = poor [blackleg data over 2 years (1999 and 2000), all other data from 1999]
**white rust resistance against race 2V and 7V, 1 = resistant As can be seen from the table, line 44A04 demonstrates very high oil content, high protein content, good saturate levels, and clearly demonstrates a unique combination of agronomic traits (including a combination of very high yield, very early maturity, short plant stature, high seed weight, low green seed content, and excellent disease resistance) that make it an important line for its area of adaptation.

Deposits

A deposit of the seed of the new 44A04 canola line is and has been maintained by Pioneer Hi-Bred International, Inc., 800 Capital Square, 400 Locust Street, Des Moines, Iowa 50309-2340, since prior to the filing date of this application. Access to this deposit will be available during the pendency of the application to the Commissioner of Patents and Trademarks and persons determined by the Commissioner to be entitled thereto upon request. Upon allowance of any claim in the application, the Applicant(s) will make available to the public pursuant to 37 CFR §1.808, sample(s) of the deposit of at least 2,500 seeds of the 44A04 cultivar with the American Type Culture Collection (ATCC), Manassas, Va. 20110-2209, ATCC Deposit No. PTA-5161, deposited Apr. 25, 2003. This deposit of the 44A04 line will be maintained in the ATCC Depository, which is a public depository, for a period of 30 years, or 5 years after the most recent request, or for the enforceable life of the patent, whichever is longer, and will be replaced if it ever becomes nonviable during that period. More specifically, 44A04 seeds of the 44A04 line were deposited under the terms of the Budapest Treaty at the ATCC on 44A04 where they have been assigned ATCC Accession No. PTA-5161. Additionally, Applicant(s) have satisfied all the requirements of 37 C.F.R. §§1.801–1.809, including providing an indication of the viability of the sample upon deposit. Applicant(s) have no authority to waive any restrictions imposed by law on the transfer of biological material or its transportation in commerce. Applicant(s) do not waive any infringement of their rights granted under this patent or under the Plant Variety Protection Act (7 U.S.C 2321 et seq.).

The foregoing invention has been described in detail by way of illustration and example for purposes of exemplification. However, it will be apparent that changes and modifications such as single gene modifications and mutations, somaclonal variants, variant individuals selected from populations of the plants of the instant line, and the like, likewise are considered to be within the scope of the present invention. All references disclosed herein whether to journal, patents, published applications and the like are hereby incorporated in their entirety by reference.

What is claimed is:

1. A canola seed of line designated 44A04, representative seed of said canola line 44A04 having been deposited under ATCC Accession No. PTA-5161.

2. A canola plant, or parts thereof, produced by growing the seed of claim 1.

3. A tissue culture of regenerable cells from the plant of claim 2.

4. A canola plant, or parts thereof, having all the physiological and morphological characteristics of canola line 44A04, representative seed of said line having been deposited under ATCC Accession No. PTA-5161.

5. A tissue culture of regenerable cells from the plant of claim 4.

6. A method for producing a first generation (F1) 44A04 progeny canola plant, comprising:

(a) crossing the canola plant or its parts of claim 4, with a second canola plant to yield progeny canola seed;

(b) growing said progeny canola seed, under plant growth conditions, to yield said first generation (F1) 44A04 progeny canola plant.

7. A method for producing a male sterile canola line comprising:

crossing the canola plant of claim 2 with a second canola plant to yield progeny canola seed, wherein the second canola plant has cytoplasmic male sterility and growing said progeny canola seed to yield an F1 male sterile canola plant.

* * * * *

UNITED STATES PATENT AND TRADEMARK OFFICE
CERTIFICATE OF CORRECTION

PATENT NO. : 6,734,345 B1
DATED : May 11, 2004
INVENTOR(S) : Gambacher et al.

It is certified that error appears in the above-identified patent and that said Letters Patent is hereby corrected as shown below:

Column 21,
Line 24, should read -- A deposit of the seed of the new 44A04 cultivar is and --
Line 31, should read -- claims in the appplication, the Applicant(s) will make avail- --
Line 32, should read -- able to the public pursuant to 37 CFR § 1.808, sample(s) of --
Line 36, should read -- VA 20110-2209, ATCC Deposit No. PTA-5161, deposited --
Line 37, should read -- April 25, 2003. This deposit of the 44A04 line will be --

Signed and Sealed this

Third Day of August, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,734,345 B1
DATED : May 11, 2004
INVENTOR(S) : Grombacher et al.

It is certified that error appears in the above-identified patent and that said Letters Patent is hereby corrected as shown below:

Column 21,
Line 31, should read:
-- claims in the application, the Applicant(s) will make avail- --

Signed and Sealed this

Sixteenth Day of November, 2004

JON W. DUDAS
*Director of the United States Patent and Trademark Office*